United States Patent [19]
Ellis

[11] Patent Number: 6,084,407
[45] Date of Patent: Jul. 4, 2000

[54] SYSTEM FOR MEASURING TISSUE SIZE AND MARBLING IN AN ANIMAL

[75] Inventor: James S. Ellis, Broomfield, Colo.

[73] Assignee: Pheno Imaging, Inc., Broomfield, Colo.

[21] Appl. No.: 09/151,234

[22] Filed: Sep. 10, 1998

[51] Int. Cl.[7] ...................................................... G01V 3/00
[52] U.S. Cl. ........................ 324/300; 324/300; 600/443
[58] Field of Search .......................... 324/300; 264/227; 600/443

[56] References Cited

U.S. PATENT DOCUMENTS

| | | | |
|---|---|---|---|
| 4,668,457 | 5/1987 | Nakai et al. | 264/227 |
| 5,398,290 | 3/1995 | Brethour | 382/6 |
| 5,520,183 | 5/1996 | Lake et al. | 128/660.01 |
| 5,613,493 | 3/1997 | Schafer | 128/660.06 |
| 5,673,647 | 10/1997 | Pratt | 119/51.02 |
| 5,836,880 | 11/1998 | Pratt . | |

OTHER PUBLICATIONS

Ville et al An Evaluation of Ultrasound and nuclear magnetic resonance spectroscopy to measure in vivo intramuscular fat content of longissimus muscle of pigs. J. Anim. Sci. 1997 75:2942–2949.

Barany et al Quqntitative and qualitative fat analysis in human leg muscle of neuromuscular diseases by 1H Spectroscopy in vivo. Mag. Reso. Med. 1989, 10 : 210–226.

Mitchell et al, Application of NMR spectroscopy and imaging for body composition analysis as related to sequential measurement of energy deposition. 12th energy symposium of farm animals. Kartausen–Ittinger. 1991, Sep., pp. 4–7 (paper).

Wilson, Doyle E., Rouse, Gene H., Hays, Craig L., Tait, J.R., and Kruser, Jodi, Scanning to the Future with Iowa State University, Department of Animal Science, Ames, Iowa, 1998.

*Primary Examiner*—Christine Oda
*Assistant Examiner*—Brij B. Shrivastav
*Attorney, Agent, or Firm*—James R. Young

[57] ABSTRACT

A computerized system scans an animal using Magnetic Resonance Imaging (MRI) to produce digital pixel values representing internal tissue. The pixel values are coded as gray scale values representing of the density of tissue scanned. The computer system then classifies each pixel, based upon its gray scale value, as representing fat, muscle, cartilage or skeletal tissue. Once classified, the percentage of intramuscular fat is calculated and presented on the screen of the computer system. Once the pixel data is classified, a perimeter around the muscle being scanned is defined by separating the muscle tissue from the surrounding tissue, and, the area of the muscle is calculated and presented to the user of the system. Multiple scans are performed along one dimension of the animal to determine the volume of the muscle. The system also ranks the animal with animals of like kind.

18 Claims, 10 Drawing Sheets

SYSTEM FOR MEASURING TISSUE SIZE AND MARBLING IN AN ANIMAL

FIELD OF THE INVENTION

This invention relates to animal measuring systems and more particularly to measuring skeletal, intramuscular fat, back fat and muscle tissue contained within a live animal or carcass. Even more particularly, the invention relates to measuring skeletal, intramuscular fat, back fat and muscle tissue through Magnetic Resonance Imaging systems.

BACKGROUND OF THE INVENTION

People have always made visual appraisals of domestic animals and humans to compare like kinds and to try to predict future performance and production. In domestic animals it is also beneficial to select a young offspring that will produce a superior animal. Animal breeders continually try to select for faster or stronger horses, increased volumes of meat for cattle, swine, poultry and sheep as well as a larger volume of milk for dairy animals. The very economic base of pricing for animals is directly related to a predicted future performance or production of the animals.

It is well known that the highest price is paid for the butchered beef carcasses that not only possess the greatest quantity of meat but also the highest percentage of intramuscular fat, which is often referred to as "marbling". The United States Department of Agriculture (U.S.D.A.) uses a grading system to compare like kinds of meat. The grading system within the beef industry denotes the highest quality meat with a rating of U.S.D.A. PRIME. Respectively the next two ratings are CHOICE and SELECT. PRIME meat brings the highest price per pound. The other end of the spectrum has the lowest ratings of CUTTER and CANNER and bring the lowest price per pound. The finest steaks (and highest priced) are often purchased by restaurants and promoted as U.S.D.A. PRIME Beef. Many of the steaks purchased in a meat market are graded U.S.D.A. CHOICE or SELECT.

When a beef animal is butchered and the actual quantity and quality of meat inside can be seen, then the grading and pricing can be very accurate. However, there is a tremendous need to determine the potential quantity and quality of the meat when the animal is younger, many months prior to butchering. A beef animal is often sold on several occasions throughout its life before it is butchered. It may be sold as a weanling (just weaned from its mother cow) and then may be sold again months later to a feed lot. In the feed lot the beef animal is given a concentrated ration of food to maximize the growth process as well as maximize the marbling within the meat. Finally, the beef animal is marketed to a butchering facility to provide steaks, roast, hamburgers and many other beef products.

The beef animal is usually weighed at each point of sale and often subjectively appraised by a person knowledgeable in the beef industry. Unfortunately, this means of appraising the beef animal doesn't provide either the buyer or the seller with an evaluation of the marbling of the meat inside the beef animal. For example, one might raise ten beef calves that on sale day each weigh the same and visually (or actually measured) appear to be nearly identical in conformation. Later, the ten are sold to a feed lot and weigh the same as well as appear similar in conformation. When they are sold to be butchered, again, the ten weigh and appear identical but the U.S.D.A. grading finally comes into play. It is possible that the meat from one animal will be rated PRIME, the meat from three others rated CHOICE and the meat from the last six will be graded SELECT. Any combination of grading is possible after butchering, but at previous sales there was no premium paid for the potential PRIME animal(s) nor was anyone able to predict which animal would be PRIME, CHOICE, or SELECT.

There have been several means attempted to measure beef muscles and intramuscular fat. Some prior art systems use x-rays and/or CAT scans for measuring. These methods have several drawbacks. Often the animal cannot remain motionless for the duration of the scan, which could take several minutes. Also, the technician(s) are required to wear protective (i.e. lead-vest) x-ray gear when x-ray scanning is used.

Other prior art systems have been developed using various types of Ultrasound (and/or sonogram) imaging. See, for example, U.S. Pat. No. 5,398,290 entitled "System for Measurement of Intramuscular Fat in Cattle" of Brethour, issued Mar. 14, 1995. Even though the scanning time of real-time ultrasound is less than that of x-rays or CAT scans, these systems still have limitations. A liquid solution must be used between the ultrasound scanning device and the animal's hide to allow transmission of the sound waves into the animal's muscle that is targeted for measuring. Several hundred beef animals passing through an area (i.e. chute) used for scanning can possibly create a slippery mess of solution on the floor. Additionally, the resulting ultrasound images may need to be interpreted by a highly skilled technician and inaccuracies are possible.

It is thus apparent that there is a need in the art for an improved method or apparatus which provides information about the size and marbling of the animal's muscles while removing requirements for a sound conducting liquid, and while reducing the skill required to operate the system. The present invention meets these and other needs in the art.

SUMMARY OF THE INVENTION

It is an aspect of the present invention to provide information about the percentage of intramuscular fat, called marbling, of meat inside a live animal or a carcass.

It is another aspect of the invention to provide information about the size of muscles within a live animal or a carcass.

Another aspect of the invention is to provide such marbling and size information without requiring interpretation by a skilled technician.

Still another aspect of the invention is to provide information about the thickness of back fat within a live animal or carcass.

A further aspect of the invention is to grade and classify animals after analyzing the intramuscular fat, back fat and muscle size within the animal.

The above and other aspects of the invention are accomplished in a computerized system that scans the animal using Magnetic Resonance Imaging (MRI). The scan data is analyzed within the computer to determine the marbling of the muscle scanned. The scan is further analyzed to determine the size of the muscle scanned.

The scan data is produced as digital pixel values within scan wave lines. The pixel values are coded as gray scale values wherein the gray scale value of each pixel is representative of the type of tissue scanned. The computer system thus classifies each pixel, based upon its gray scale value, as representing fat, cartilage, muscle or skeletal tissue. Once classified, the percentage of intramuscular fat can be calculated and presented on the screen of the computer system.

Also, once the pixel data is classified, a perimeter around the muscle being scanned can be defined by separating the muscle tissue from the fat and skeletal tissue or the surrounding muscle sheath called a fascia. Once the perimeter of the muscle is defined, the area of the muscle is calculated and presented to the user of the system.

Multiple scans can be performed along one dimension of the animal so that the volume of the muscle can be calculated.

Once the intramuscular fat and muscle size and volume have been determined for a particular animal, the animal is graded and classified for ranking within like kinds of animals.

BRIEF DESCRIPTION OF THE DRAWINGS

The above and other aspects, features, and advantages of the invention will be better understood by reading the following more particular description of the invention, presented in conjunction with the following drawings, wherein.

DESCRIPTION OF THE PREFERRED EMBODIMENT

The following description is of the best presently contemplated mode of carrying out the present invention. This description is not to be taken in a limiting sense but is made merely for the purpose of describing the general principles of the invention. The scope of the invention should be determined by referencing the appended claims.

Figure 1:
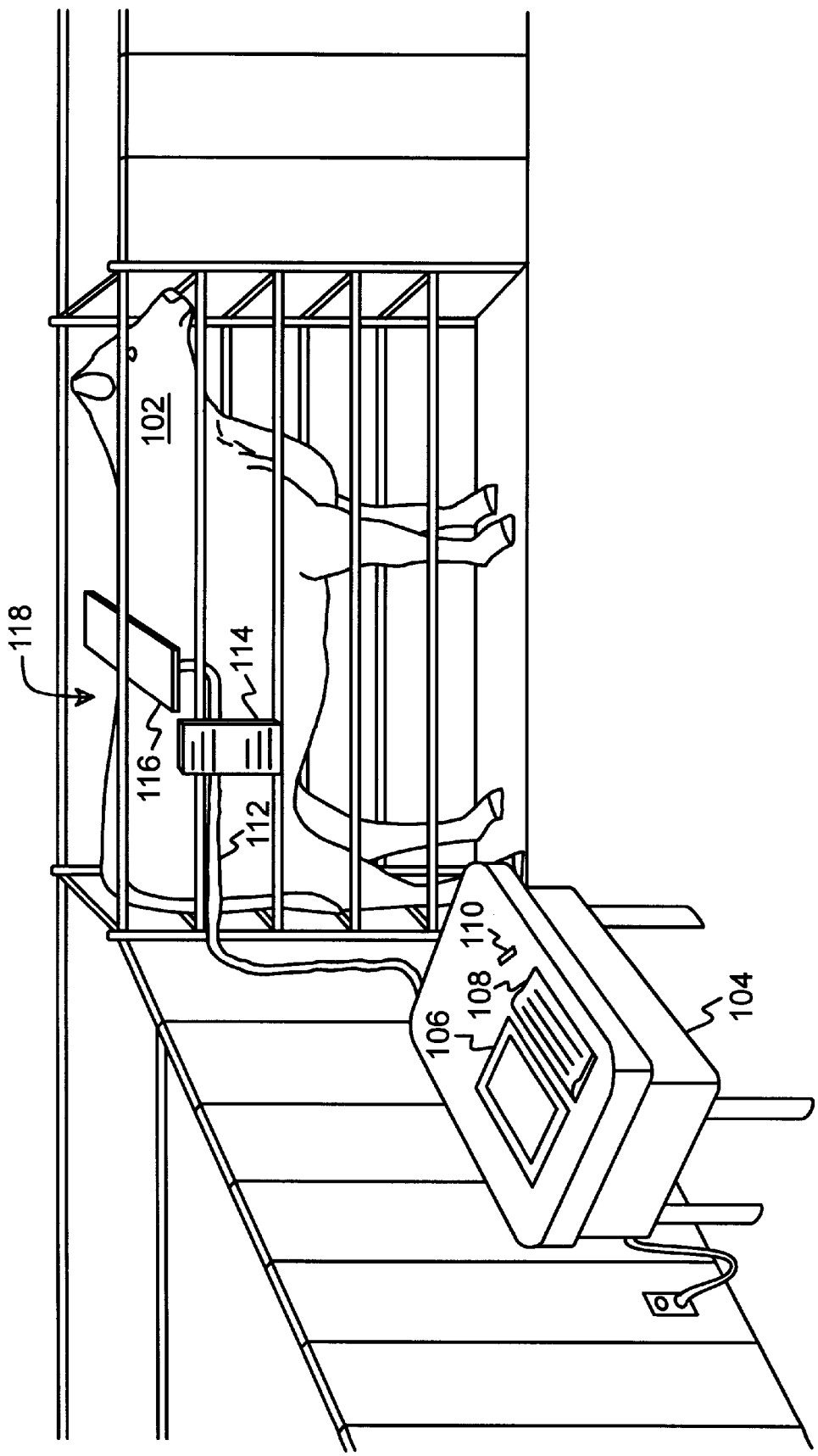
FIG. 1 shows an animal being measured using the present invention.

FIG. 1 shows an animal being measured using the present invention. Referring to FIG. 1, a chute 118 is used to contain an animal 102 being measured by the present invention. Alternatively, the animal could be standing at halter, or simply standing freely. A computer system 104 is shown having a display 106, keyboard 108 and mouse 110. This is a conventional personal computer system, which is commonly used. Cable 112 connects the computer system to the MRI scanner parts 114 and 116. Part 114 typically contains the electronics of the MRI scanner, and part 116 contains the scanning element that is placed over the animal. An example of this type of MRI system can be found in U.S. Pat. No. 5,304,930 entitled "Remotely Positioned MRI System", issued Apr. 19, 1994 to Crowley, et al.

The MRI scanning element 116 can be placed at any location over the animal 102, and precisely located as desired. Also, scanning element 116 can be placed on a movable apparatus (not shown), controlled by the computer system 104, that allows the scanning element 116 to be moved along the length of the animal to obtain the multiple scans needed to perform muscle volume measurements, as described below. Once the scanning element 116 is in place, the mouse 110, or other switch device (not shown), is used to start a scan, which typically takes less than one second. Should the animal 102 move during the scan, the operator can re-scan so as to get a correctly focused scan.

Once the scan is complete, computer system 104 analyzes the MRI wave lines to determine the marbling percentage, size of the muscle, and thickness of back fat located underneath the scanning element 116, as will be described below. After analyzing these traits, the computer system 104 grades and classifies the animal to rank it within like kinds of animals.

Once the animal is graded, the computer system 104 can direct the animal to different holding pens by opening a gate into the selected holding pen.

As an alternative to producing digital data directly from the MRI scanning device, an MRI scan can produce a photographic media print or negative, which is then scanned and digitized using a conventional scanner.

Figure 2:
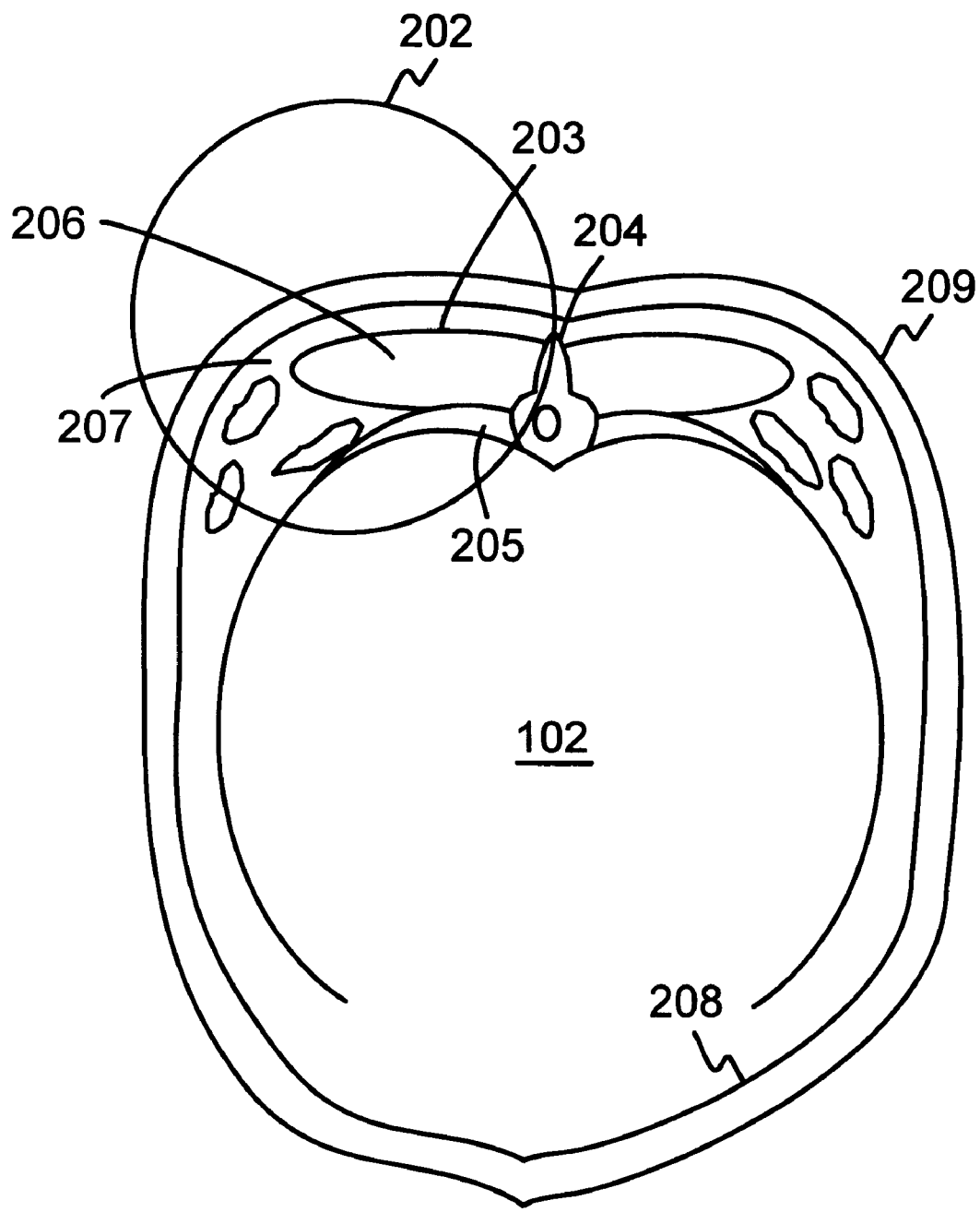
FIG. 2 shows a cross section of a beef animal, illustrating an area for measurement with the present invention.

FIG. 2 shows a cross-sectional view, taken between the twelfth and thirteenth ribs, of the animal 102 (FIG. 1) and illustrates the location where the scan is typically taken in a beef animal. Referring to FIG. 2, circle 202 illustrates the location for a typical MRI scan, which would produce data showing the structure of the muscle fascia 203, the spine 204, cartilage between the ribs 205, muscle area 206, back fat 207, hide 208 and hair 209 of the animal 102.

Figure 3:
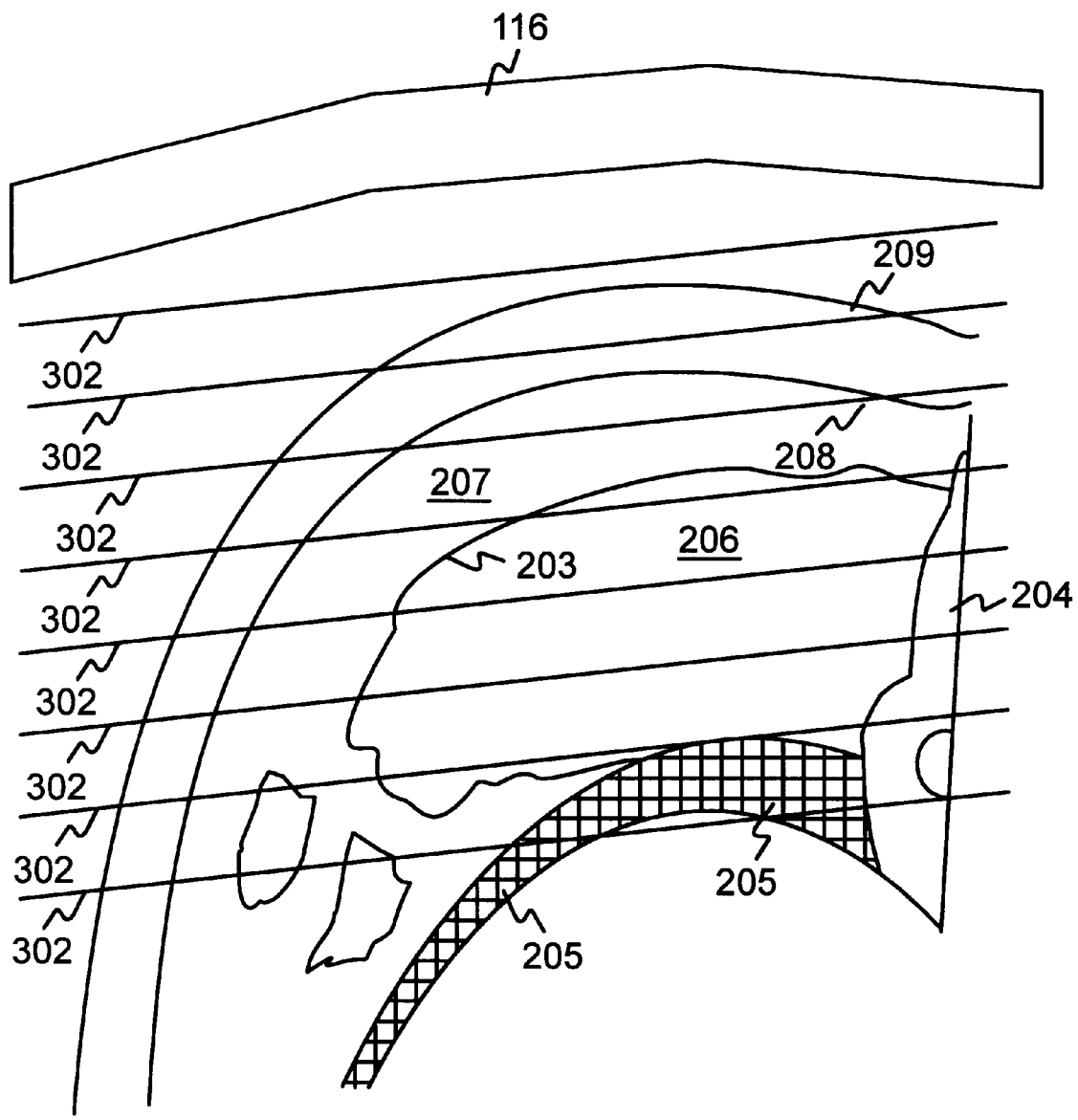
FIG. 3 shows a cross-section of a beef animal, and shows MRI Wave lines where an MRI scanner produces data of the texture of the muscle, fascia, fat and skeletal structure of the beef animal.

FIG. 3 shows the area 202 and illustrates the MRI scan wave lines. Referring to FIG. 3, the MRI scan, created from the scanner element 116, produces a plurality of scan wave lines 302 which capture data about the fascia 203, spine 204, muscle 206, cartilage 205, located between the ribs, back fat 207, hide 208 and hair 209 of the animal being scanned. The wave lines 302 extend throughout the tissue area being scanned. A magnetic field of 0.5 to 1.5 tesla can be used to produce the scan wave lines 302. Producing one wave line takes approximately one twentieth of one second, so producing the eight wave lines shown take less than one half of one second. Additional scan lines could be produced, and the scan lines produced closer together, to scan any desired percentage of the muscle, up to 100 percent. Producing additional wave lines takes additional time, however, additional wave lines could be used to produce additional accuracy in the estimate of the marbling and size of the muscle. As more time is taken, to produce a higher number and/or density of wave lines, the probability that the animal will move increases, but a complete scan is possible if the animal does not move, which is possible for some docile animals or by restraining the any animal. In the preferred embodiment of the invention, less than ten wave lines are produced, requiring less than one half of one second. Also, when an MRI scan is performed, the distance between the scan wave lines is set within the MRI scanner, so the depth of the tissue scanned by ten wave lines is therefore also adjustable.

Figure 4:
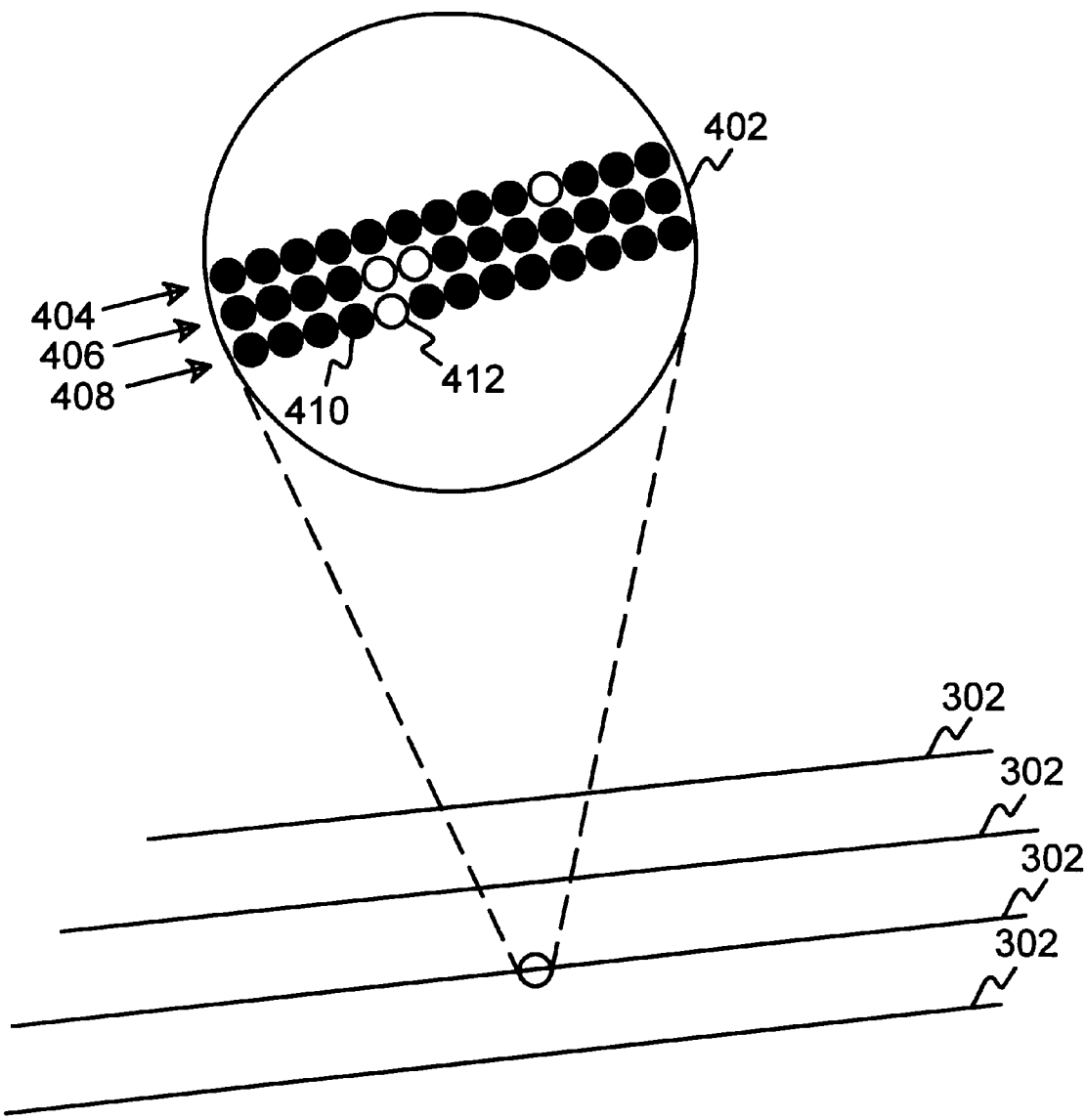
FIG. 4 illustrates pixels from an MRI wave line, and further illustrates which pixels are muscle and fat.

FIG. 4 shows one of the scan wave lines, and illustrates the pixel data that is returned to the computer system 104 as part of a scan wave line. Referring to FIG. 4, the scan wave lines 302 are shown as they were produced by the scan shown in FIG. 3. The area 402 is an enlarged illustration of the pixels that are part of one of the scan wave lines. Within the area 402, three rows of pixels, labeled 404, 406, and 408, are shown. Three rows of pixels is by way of example only, since the number of pixels located within a scan wave line is variable, depending upon the setting of the MRI scanner. Additionally, many pixels can be combined into a cluster of pixels, for example by averaging gray scale values of all the pixels within each cluster, and the cluster analyzed instead of analyzing individual pixels.

Within the row 408, pixel 410 illustrates muscle tissue, and pixel 412 illustrates intramuscular fat. Typically each of the pixels is returned as a gray scale level, and as discussed above several pixels may be combined before analysis to produce a combined gray scale level. The gray scale level for each pixel is analyzed to separate each into a pixel that represents muscle tissue, a pixel that represents fat tissue, a pixel that represents cartilage, or a pixel that represents skeletal tissue, wherein the separation is based upon the range of gray scale levels typically found for each of the type of tissues within the type of animal scanned. Also, a large sequence of fat or skeletal pixels could be ignored, if they are located on the periphery of the ribeye muscle, assuming that they represent a large fat area that would be trimmed from the meat, or they represent a bone, that would be trimmed from the meat. The remaining pixels are counted and the ratio of intramuscular fat pixels to muscle pixels is calculated and this ratio converted to a percentage of marbling.

Figure 5:
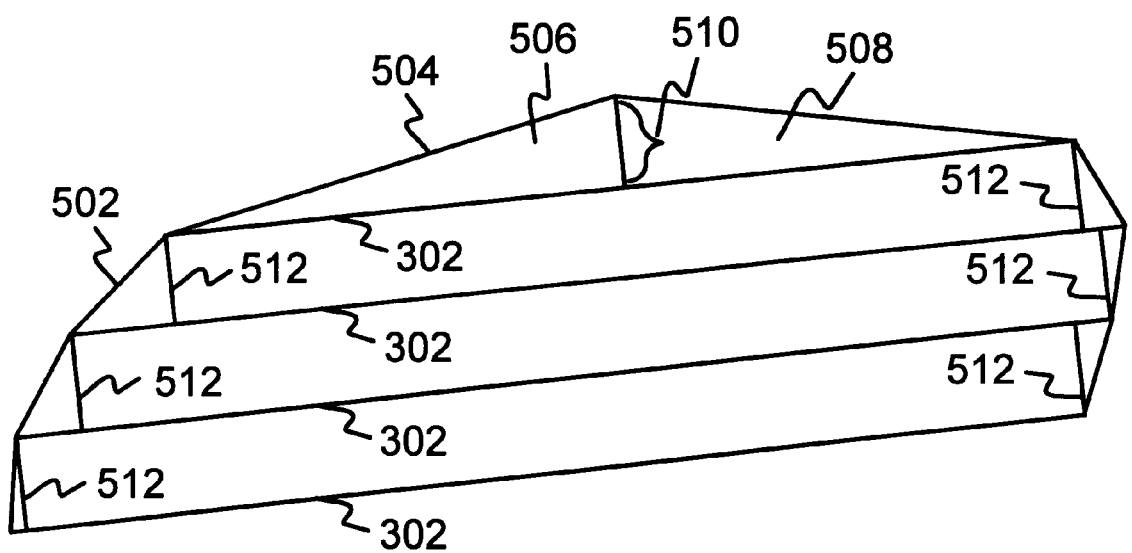
FIG. 5 illustrates how an area of a muscle is determined.

FIG. 5 shows a cross-section and illustrates calculating an area of the muscle. Referring to FIG. 5, scan wave lines 302 are shown with an outline 502 around the ribeye (longissimus dorsi) muscle. Each scan wave line 302 is terminated by analyzing the pixels, as illustrated in FIG. 4, by terminating a line when a series of fascia, fat or skeletal pixels are found. That is, the line is examined, pixel by pixel, from the center of the line outward, and the end of the line is set at the beginning of a long series of fascia, fat, or skeletal pixels. The length of the series of fascia, fat, or skeletal pixels necessary to terminate a scan wave line is typically ten to twenty pixels, although this is variable depending upon the density of the scan, the type of muscle and the type of animal. Once the termination points of each scan wave line are fixed, the length of the scan wave line is calculated as the distance between the termination points.

The outline 502 is created by connecting the ends of the scan wave lines 302. The line 504 is located by using the center of the uppermost scan wave line and extending upward a distance 510 equal to one-half the distance between scan wave lines, then forming two right triangles 506 and 508.

A line 512 is extended from each end of each scan wave line to the next scan wave line below. The two scan wave lines and the two extended lines thus form a rectangle. A right triangle is formed at the end of each rectangle by connecting the extended line, the remaining part of the longer scan wave line and the ends of the two scan wave lines. The area between the two lines is calculated by calculating the area of the rectangle and the two right triangles. After the area between all the scan lines is calculated, the areas, including right triangles 506 and 508 are summed to get the total area of the ribeye muscle.

If the volume of the muscle is desired, multiple MRI scans are made, using a fixed distance between the scans. By calculating the area of the muscle at each scan, and calculating the volume between each scan in the same manner as the area is calculated, the volume of the muscle can be calculated.

In a similar manner, the thickness of the fat area between the muscle and the hide of the animal can be calculated as described below with respect to FIGS. 8 and 9.

Because the hide of a beef animal is denser than the fat or muscle, and differs in density from the skeletal structure, the thickness of the hide can also be determined using these methods.

Figure 6:
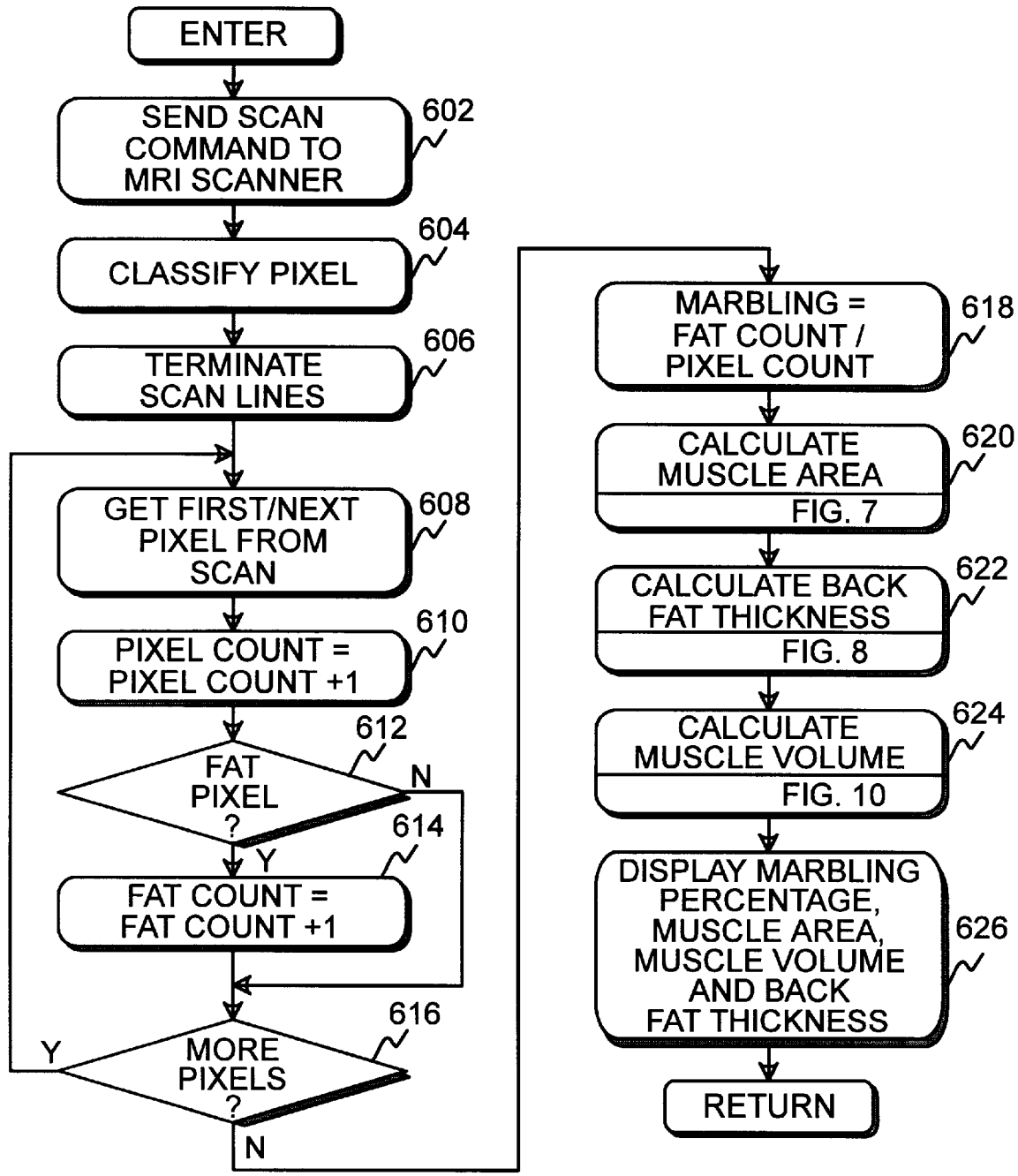
FIG. 6 shows a flowchart of the process of scanning an animal and calculating a percentage of marbling within the tissue of the animal.

FIG. 6 shows a flowchart of the process of the invention for determining the marbling and area of the muscle. This flowchart is called within scanner software contained in the computer system 104 (FIG. 1) when the operator requests a scan after the scanner has been positioned over the desired part of the animal. Referring to FIG. 6, after entry, step 602 sends a command to the scanner to perform a scan. After the scan is complete, and the scan data is returned to the computer system 104, step 604 classifies all the pixels found, as described above, and step 606 terminates the scan lines by removing the pixels that represent fat, cartilage or skeletal tissue at the ends of the scan lines, as described above with respect to FIG. 5. Step 608 gets the first pixel of the first scan wave line from the scan data. Step 610 adds this pixel to the pixel count. Step 612 determines whether the pixel represents fat, and if it does, step 612 goes to step 614 which increments the intramuscular fat count of pixels. Step 616 determines if there are more pixels to retrieve, and if so, step 616 goes back to step 606 to process the next pixel.

After all pixels have been processed, step 618 calculates the percent of marbling by dividing the intramuscular fat count of pixels by the total count of pixels, and multiplying the result by 100 to get the percentage. Step 620 then calls FIG. 7 to calculate the area of the muscle, step 622 calls FIG. 8 to get the back fat thickness, and step 624 calls FIG. 10 to get the muscle volume.

After these have been calculated, step 626 displays the marbling percentage, muscle area, back fat thickness, and muscle volume on the display 106 (FIG. 1).

Figure 7:
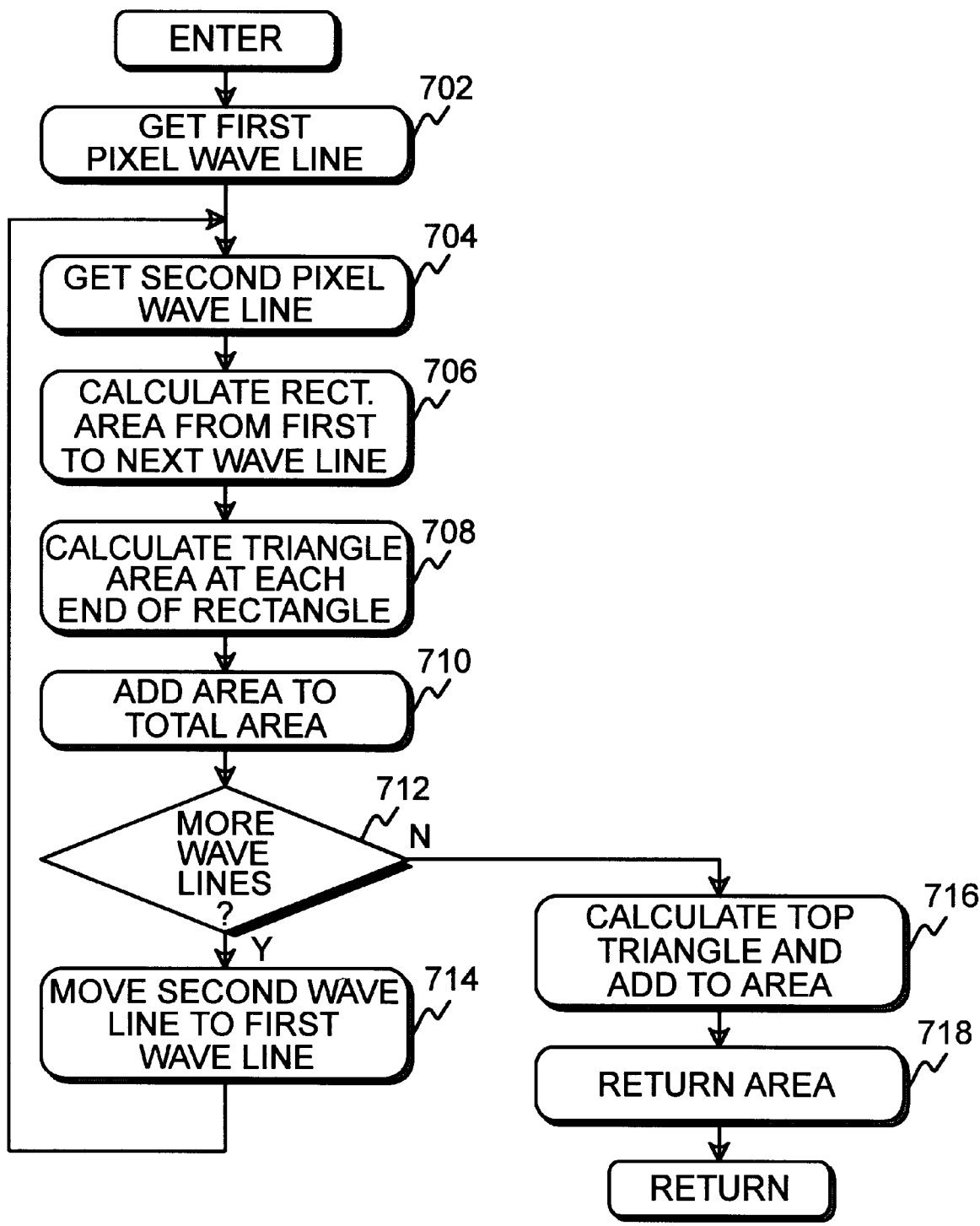
FIG. 7 shows a flowchart of the process of determining a cross-sectional area of a muscle within an animal.

FIG. 7 shows a flowchart of the process of calculating the area of the muscle, as described above with respect to FIG. 5. Referring to FIG. 7, after entry, step 702 gets the first wave line, which has already been processed, as described above with respect to step 604 (FIG. 6) and FIG. 5. Step 704 gets the next (second) wave line after the first wave line, and step 706 calculates the area of the rectangle between the two wave lines. Step 708 calculates the area of the two triangles at each end of the lines, and step 710 adds the area of the rectangle and the two triangles to the total area.

Step 712 determines if there are more wave lines in the scan, and if so, goes to block 714, which copies the second wave line to the first wave line, so that it can be used in the next calculation. Step 714 then returns to step 704 to process the next wave line.

After all wave lines have been processed, step 712 goes to step 716 which calculates the area of the two triangles at the top of the muscle, and step 718 returns the muscle area to FIG. 6, where it is displayed.

Although the invention has been described as measuring the intramuscular fat, area and volume of muscles within live animals, those skilled in the art will recognize that the invention can also be used to achieve these same measurements within the carcass of a butchered animal.

Figure 8:
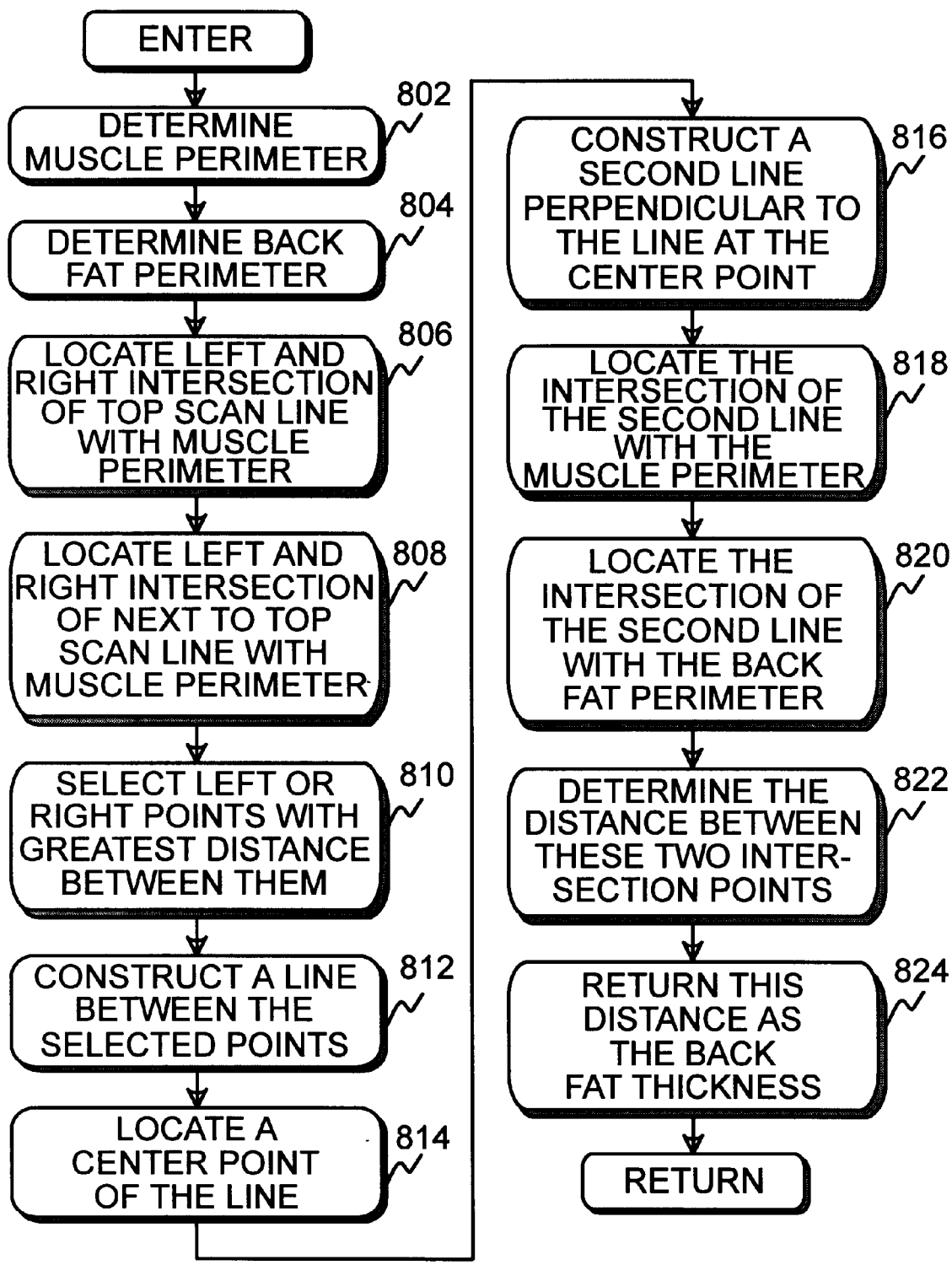
FIG. 8 shows a flowchart of the process of measuring a thickness of back fat in a beef animal.

FIG. 8 shows a flowchart of calculating the back fat thickness in a beef animal, as is called from step 622 of FIG. 6. Referring to FIG. 8, after entry, step 802 determines the outer perimeter of the muscle, as described above with respect to FIG. 5. Step 804 determines the outer perimeter of the back fat in the same manner described above to find the perimeter of the muscle. Step 806 locates the left and right intersection points of the top most scan wave line with the muscle perimeter. Step 808 locates the left and right intersection points of the next to the top most scan wave line and the muscle perimeter. Step 810 determines the distance between the two left points and the distance between the two right points and selects the set of left or right points having the greatest distance between them.

Step 812 constructs a line between the two points selected in step 810 and step 814 locates the center of the line constructed in step 812. Step 816 constructs a line perpendicular to the line constructed in step 812 at the center located in step 814 and in a direction toward the top scan wave line. Step 818 locates the intersection of the line constructed in step 816 and the muscle perimeter, and step 820 locates the intersection of the line constructed in step 816 and the back fat perimeter. Step 822 determines the distance between the intersection located in step 818 and the intersection located in step 820 and step 824 returns this distance as the back fat thickness to FIG. 6.

Figure 9:
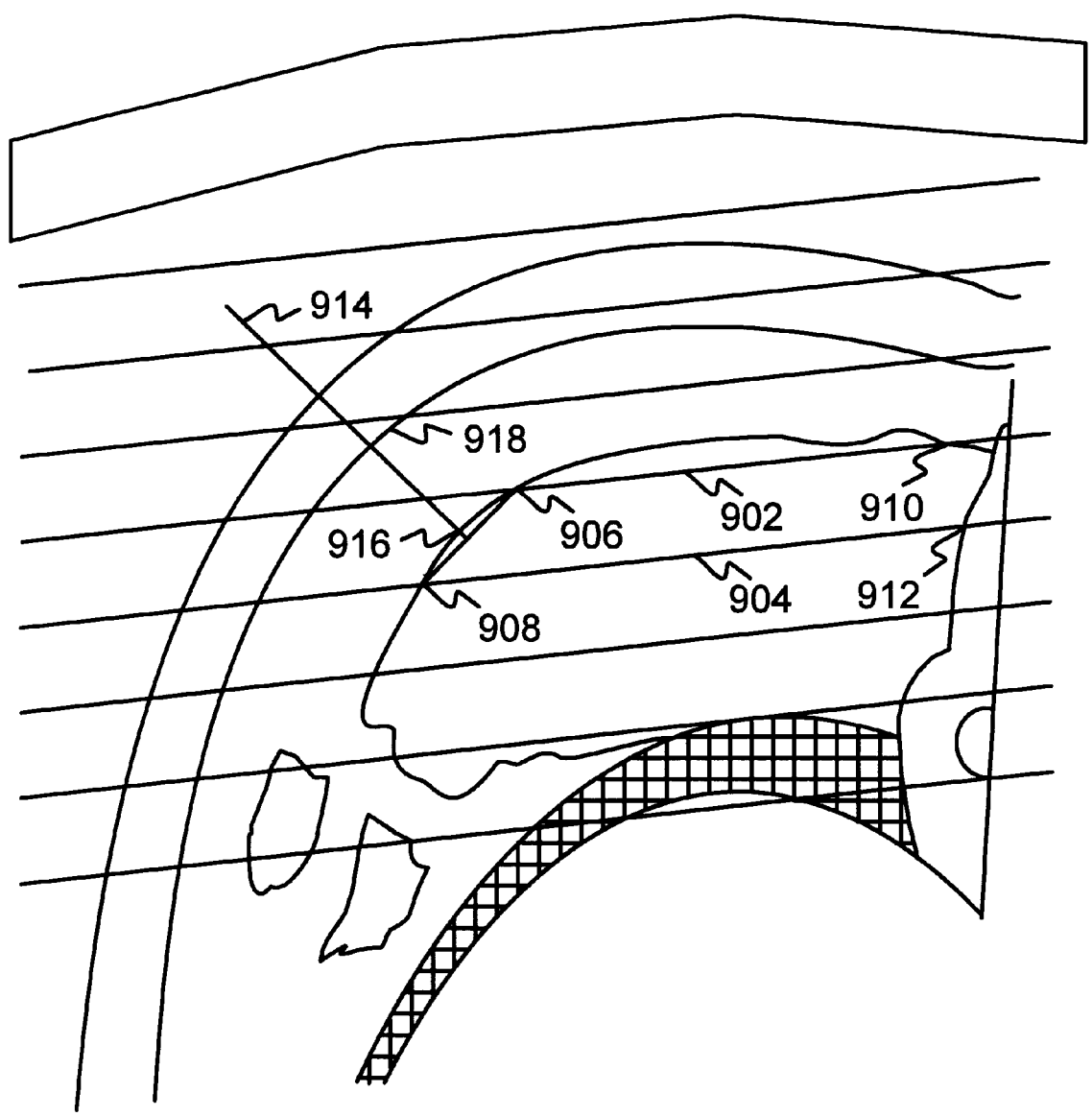
FIG. 9 illustrates the process of FIG. 8.

FIG. 9 graphically depicts the process of FIG. 8 of finding the back fat thickness. Referring to FIG. 9, wave scan line 902 is the top most wave scan line that intersects the muscle perimeter, and wave scan line 904 is the next to the top most wave scan line that intersects the muscle perimeter. Points 906 and 910 are the respective left and right intersection points of the top most wave scan line with the muscle perimeter. Points 908 and 912 are the respective left and right intersection points of the next to the top most wave scan line with the muscle perimeter. Since left points 906 and 908 are farther apart than right points 910 and 912, points 906 and 908 would be selected and a line constructed between them. The center of this line is located and a line 914 is drawn perpendicular to the line between points 906 and 908 at the center point, in a direction toward the top most scan wave line 902. The intersection 916 with this line and the muscle perimeter and the intersection 918 with this line and the back fat perimeter are located and the distance between them is the back fat thickness.

Figure 10:
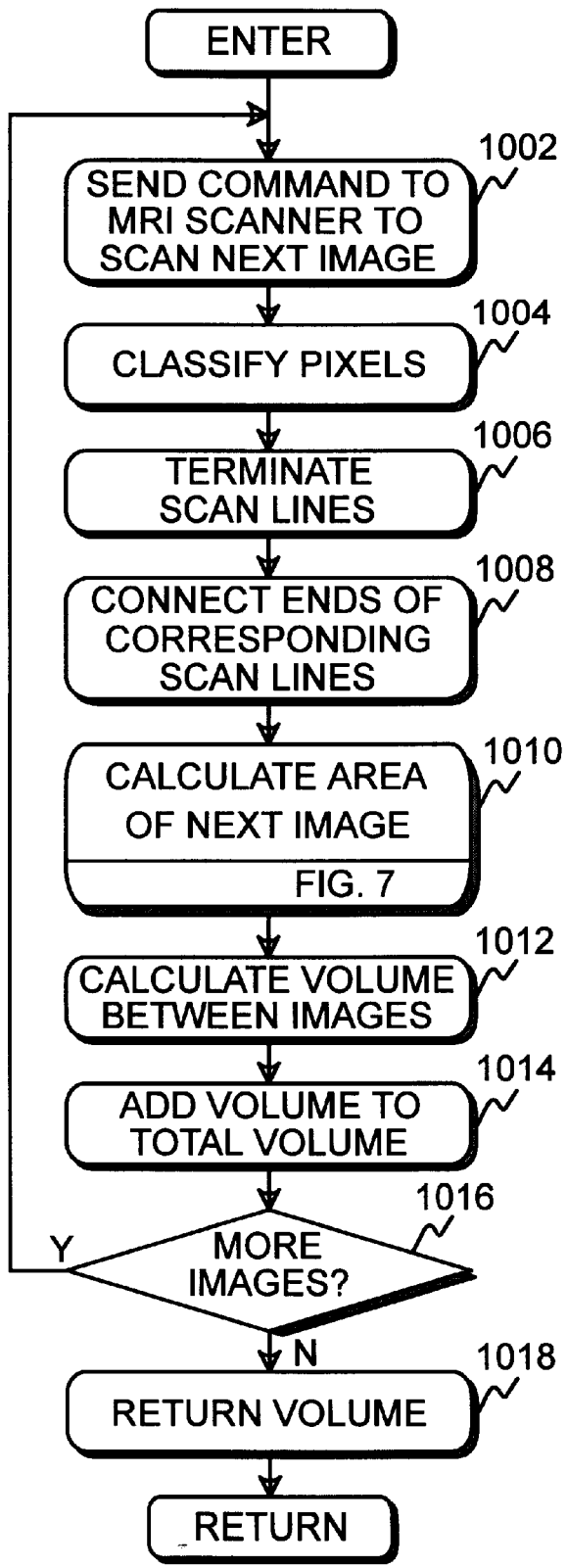
FIG. 10 shows a flowchart of the process of determining a volume of a muscle within an animal.

FIG. 10 shows a flowchart of calculating the volume of a muscle, as called from step 624 of FIG. 6. Referring to FIG. 10, after entry, step 1002 sends another command to the MRI scanner to scan another image at a known distance from the first image scanned in FIG. 6. Step 1004 classifies the pixels of the scanned data, step 1006 terminates the scan lines from the second image scanned in step 1002, and step 1008 connects the ends of corresponding scan lines from the scan performed in FIG. 6, and the scan performed in step 1002. Step 1010 calls FIG. 7 to calculate the area of the scan performed in step 1002, and step 1012 then calculates the volume between the two scan images in the same manner the areas of the images were calculated.

Step 1014 adds this volume to the total volume accumulated, and block 1016 determines if more images need to be scanned. This 20 determination is based on the size of the image scanned in step 1002, and terminates when the area of the scan becomes small enough to be the end of the muscle. It more images are needed, step 1016 returns to step 1002 to scan the next image.

After all images are scanned, and volumes calculated, step 1016 returns the volume to FIG. 6 for display.

Having described a presently preferred embodiment of the present invention, it will be understood by those skilled in the art that many changes in construction and circuitry and widely differing embodiments and applications of the invention will suggest themselves without departing from the scope of the present invention, as defined in the claims. The disclosures and the description herein are intended to be illustrative and are not in any sense limiting of the invention, defined in scope by the following claims.

What is claimed is:

1. A system for measuring intramuscular fat within an animal, the system comprising:

a computer system;

a magnetic resonance imaging scanner connected to the computer system, and located adjacent an area of tissue of an animal to be scanned, wherein scan wave line pixel data, produced by the scanner, is transferred to the computer system;

scan evaluation software located within the computer system for evaluating the wave line pixel data produced by the scanner to calculate and display a percentage of intramuscular fat within the tissue scanned by the scanner;

termination software within the scan evaluation software to locate first and second termination pixels, one at each boundary between muscle tissue and the surrounding tissue within each wave line;

intramuscular fat determination software, within the scan evaluation software, to calculate the percentage of intramuscular fat between the first and second termination pixels of each wave line located by the termination software; and averaging software within the scan evaluation software to average the percentage of fat found by the intramuscular fat determination software for each wave line.

2. The system of claim 1 further comprising:

perimeter connection software within the scan evaluation software for connecting the first and second termination pixels of each line, to the first and second termination pixels of an adjacent wave line, thus forming a perimeter around the muscle tissue; and area calculation software within the scan evaluation software for determining the area within the perimeter formed by the perimeter connection software.

3. The system of claim 1 further comprising:

volume perimeter software within the scan evaluation software for connecting the first and second termination pixels of respective scan lines from a plurality of scans of the tissue, wherein each scan is located at a predetermined distance from a previous scan; and volume measuring software for determining the volume of the muscle located between first and last scans of the plurality of scans.

4. A system for measuring intramuscular fat within an animal, the system comprising:

a computer system;

a magnetic resonance imaging scanner connected to the computer system, and located adjacent an area of tissue of an animal to be scanned, wherein scan wave line pixel data, produced by the scanner, is transferred to the computer system;

scan evaluation software located within the computer system for evaluating the wave line pixel data produced by the scanner to calculate and display a percentage of intramuscular fat within the tissue scanned by the scanner;

termination software within the scan evaluation software to locate first and second termination pixels, wherein the first termination pixel is located at the boundary between the muscle tissue and surrounding tissue, and the second termination pixel is located at a boundary between fat and hide within the tissue of the animal, wherein a perimeter of the back fat is located; and fat thickness determination software, within the scan evaluation software, to calculate a thickness of the back fat of the animal.

5. A system for measuring intramuscular fat within an animal, the system comprising:

a computer system;

a magnetic resonance imaging scanner connected to the computer system, and located adjacent an area of tissue of an animal to be scanned, wherein scan wave line pixel data, produced by the scanner, is transferred to the computer system;

scan evaluation software located within the computer system for evaluating the wave line pixel data produced by the scanner to calculate and display a percentage of intramuscular fat within the tissue scanned by the scanner termination software within the scan evaluation software to locate first and second termination pixels, wherein the first termination pixel is located at the boundary between the fat and hide within the tissue scanned, and the second termination pixel is located at a surface of the hide within the tissue of the animal;

hide thickness determination software, within the scan evaluation software, to calculate the length of each wave line between the first and second termination pixels of each wave line located by the termination software; and hide averaging software within the scan evaluation software to determine the average thickness of hide found by the hide thickness determination software for the wave lines.

6. A system for measuring intramuscular fat within an animal, the system comprising:

a computer system;

a magnetic resonance imaging scanner connected to the computer system, and located adjacent an area of tissue of an animal to be scanned, wherein scan wave line pixel data, produced by the scanner, is transferred to the computer system;

scan evaluation software located within the computer system for evaluating the wave line pixel data produced by the scanner to calculate and display a percentage of intramuscular fat within the tissue scanned by the scanner;

a photographic output device connected to the MRI scanner to transfer scan wave lines to a photographic negative; and scanning the photographic negative to produce the scan wave line pixel data.

7. A system for measuring intramuscular fat within an animal, the system comprising:

a computer system;

a magnetic resonance imaging scanner connected to the computer system, and located adjacent an area of tissue of an animal to be scanned, wherein scan wave line pixel data, produced by the scanner, is transferred to the computer system;

scan evaluation software located within the computer system for evaluating the wave line pixel data produced by the scanner to calculate and display a percentage of intramuscular fat within the tissue scanned by the scanner wherein said scan evaluation software further comprises classification software to rank the animal within like kinds of animals.

8. A method for measuring intramuscular fat within an animal, the method comprising the steps of:

(a) locating a scanning element of a magnetic resonant imaging scanner adjacent to a selected area of tissue of the animal to be scanned;

(b) scanning a portion of the animal with the magnetic resonance imaging scanner;

(c) transferring scan wave line pixel data, produced by the scanner, to a computer system;

(d) within the computer system, classifying each pixel within each line of the scan wave line pixel data into a first class of pixel representing muscle within the tissue scanned, and a second class of pixel representing fat within the tissue scanned;

(e) within the computer system, calculating a percentage of fat within each scan wave line as a number of the second class of pixels divided by a sum of a number of the first class of pixels plus a number of the second class of pixels times one hundred; and (f) within the computer system, averaging the percentage of fat of each of the scan wave lines and displaying this average as a percentage of intramuscular fat within the tissue scanned by the scanner.

9. The method of claim 8 wherein step (d) further comprises the following step (d1) and step (e) further comprises the following step(e1):

(d1) locating first and second termination pixels, one at each boundary between muscle tissue and surrounding tissue within each scan wave line; and (e1) calculating a percentage of intramuscular fat between the first and second termination pixels of each wave line located by the termination software.

10. The method of claim 9 further comprising the steps of:

(g) programmatically connecting the first and second termination pixels of each scan wave line, to the first and second termination pixels of each adjacent wave line, thus forming a perimeter around the muscle tissue; and (h) determining the area within the perimeter formed in step (g).

11. The system of claim 10 further comprising:

(i) programmatically connecting the first and second termination pixels of respective scan lines from a plurality of scans of the tissue, wherein each scan is located at a predetermined distance from a previous scan; and (j) determining a volume of the muscle located between first and last scans of the plurality of scans.

12. The method of claim 10, further comprising the steps of:

(g) locating first and second termination pixels within each scan wave line, wherein the first termination pixel is located at a boundary between muscle tissue and surrounding tissue within the tissue scanned, and the second termination pixel is located at a boundary between fat and hide within the tissue scanned, wherein a perimeter of back fat of the animal is located; and (h) calculating a thickness of back fat of the animal between the perimeter of the muscle and the perimeter of the back fat.

13. The method of claim 8 further comprising the steps of:

(g) locating first and second termination pixels, wherein the first termination pixel is located at the boundary between fat and hide within the tissue scanned, and the second termination pixel is located at a surface of the hide within the tissue of the animal;

(h) calculate a length of each wave line between the first and second termination pixels of each wave line located in step (g); and (i) determining an average thickness of hide found in each line in step (h) and displaying this average as the average hide thickness of the animal.

14. The method of claim 8 wherein step (b) further comprises the steps of:
   (b1) transferring scan wave line data from the magnetic resonance imaging scanner to a photographic medium; and
   (b2) scanning the photographic medium to produce the scan wave line pixel data.

15. The method of claim 8 further comprising the step of:
   (g) ranking the animal by percentage of intramuscular fat within like kinds of animals.

16. The method of claim 8 wherein step (e) further comprises the step of grouping the pixels of the scan wave line into a plurality of clusters of pixels, wherein a grayscale value for each cluster is an average of the grayscale values of each of the pixels and further wherein clusters of pixels are used to determine the percentage of intramuscular fat.

17. A method for measuring dimensions of tissue within an animal, the method comprising the steps of:
   (a) locating a scanning element of a magnetic resonant imaging scanner adjacent to a selected area of tissue of the animal to be scanned;
   (b) scanning a portion of the animal with the magnetic resonance imaging scanner;
   (c) transferring scan wave line pixel data, produced by the scanner, to a computer system;
   (d) within the computer system, classifying each pixel within each line of the scan wave line pixel data into a first class of pixel representing muscle tissue within the tissue scanned, and a second class of pixel representing fat tissue within the tissue scanned;
   (e) within the computer system, locating first and second termination pixels, one at each end of muscle tissue within each scan wave line;
   (f) within the computer system, connecting the first and second termination pixels of each scan wave line, to the first and second termination pixels of each adjacent wave line, thus forming a perimeter around the muscle tissue; and
   (g) within the computer system, determining the area within the perimeter formed in step (f).

18. The method of claim 17 further comprising the steps of:
   (h) within the computer system, calculating a percentage of fat within each scan wave line as a number of the second class of pixels divided by a sum of the number of the first class of pixels and the number of the second classes of pixels, and then multiplying by one hundred; and
   (f) within the computer system, averaging the percentage of fat of each of the scan wave lines and displaying this average as a percentage of intramuscular fat within the tissue scanned by the scanner.

* * * * *